United States Patent [19]

Frosch et al.

[11] Patent Number: 4,847,408

[45] Date of Patent: Jul. 11, 1989

[54] PROCESS FOR THE PREPARATION OF (CYCLO)ALIPHATIC DIISOCYANATES

[75] Inventors: Hans-Georg Frosch, Cologne; Heinrich Grave, Bergisch-Gladbach; Herbert Stutz, Dormagen; Eckart Waldau, Duesseldorf; Peter Fuhrmann, Cologne, all of Fed. Rep. of Germany

[73] Assignee: Bayer Aktiengesellschaft, Leverkusen, Fed. Rep. of Germany

[21] Appl. No.: 185,721

[22] Filed: Apr. 25, 1988

[30] Foreign Application Priority Data

Apr. 30, 1987 [DE] Fed. Rep. of Germany ....... 3714439

[51] Int. Cl.$^4$ ........................................... C07C 118/00
[52] U.S. Cl. .................................................... 560/347
[58] Field of Search ......................................... 560/347

[56] References Cited

U.S. PATENT DOCUMENTS 3,226,410 12/1965 Hettich et al. ...................... 560/347

FOREIGN PATENT DOCUMENTS 6567268 8/1951 Fed. Rep. of Germany.
1165831 10/1969 United Kingdom.

OTHER PUBLICATIONS

Ullmanns 4th Edition, vol. 13, p. 353.
Chemical Abstracts CA 48, 8747, 10634, 1954.

*Primary Examiner*—Alan Siegel
*Attorney, Agent, or Firm*—Gene Harsh; Joseph C. Gil; Thomas W. Roy

[57] ABSTRACT

The present invention relates to a process for the preparation of diisocyanates corresponding to the formula

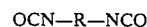

OCN—R—NCO wherein
R denotes a (cyclo)aliphatic hydrocarbon group with up to 15 carbon atoms by phosgenation of the corresponding diamines represented by the formula

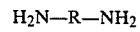

H$_2$N—R—NH$_2$ in the gas phase, characterized in that
(a) the diamines in vapor form, optionally diluted with an inert gas or with the vapors of an inert solvent, and phosgene are separately heated to temperatures of about 200° to 600° C. and continuously reacted together in a cylindrical reaction chamber which is free from moving parts and heated to about 200° to 600° C., while a turbulent flow is maintained in the reaction chamber.
(b) the gas mixture continuously leaving the reaction chamber is passed through an inert solvent for the diisocyanate which is maintained at a temperature above the decomposition temperature of the carbamic acid chloride corresponding to the diamine, and
(c) the diisocyanate which is dissolved in the inert solvent is purified by distillation.

6 Claims, No Drawings

PROCESS FOR THE PREPARATION OF (CYCLO)ALIPHATIC DIISOCYANATES

BACKGROUND OF THE INVENTION

1. Field of the Invention

This invention relates to a new process for the preparation of (cyclo)aliphatic diisocyanates by the phosgenation of (cyclo)aliphatic diamines in the gas phase.

2. Description of the Invention

The preparation of isocyanates by the reaction of amines with phosgene in the gas phase has been known for a long time (see Siefken, Annalen 562, 108 (1949)), but gas phase phosgenation has hitherto achieved technical importance only for the reaction of monoamines because polyfunctional amines partly decompose on evaporation and tend to form polymers during phosgenation (see Ullmann, 4th Edition, Vol. 13, page 353), so that the yields obtained are generally low.

A process in which hexamethylenediamine is reacted with phosgene in the gas phase in the presence of nitrogen and benzene to form hexamethylene diisocyanate is described in DE-PS No. 870 847. The yield obtained is approximately 10 to 15% of the theoretical yield. This unsatisfactory yield is a disadvantage of the process.

Two publications (J. Chem. Soc. Japan, Ind. Chem. Sect. 55, 266-7 (1952) and Ibid. 56, 289-290 (1953)) describe the gas phase synthesis of isocyanates in which the amine evaporates off together with toluene and is reacted in the gas phase with a stoichiometric excess of phosgene, amounting to 130% of the theoretical quantity, in a tube reactor at temperatures of at most 325° C. The isocyanate in vapor form is condensed in toluene, but parts of the isocyanate react with hydrogen chloride to form solid carbamic acid chloride in the process. To convert the carbamic acid chloride into the desired isocyanate, the suspension of carbamic acid chloride in toluene is heated under reflux until no more hydrogen chloride evolves. The reaction of hexamethylenediamine by this process at 280° C. to 300° C. results in a yield of 80%. The disadvantages of this process lie in the low yield and the cost intensive thermal decomposition of the carbamic acid chloride. Both these disadvantages would appear to render the process uneconomical.

GB-P No. 1 165 831 describes inter alia a process for the gas phase phosgenation of diisocyanates in which the reaction of the amine in vapor form with phosgene is carried out at temperatures of 150° to 300° C. in a tube reactor equipped with mechanical stirrer. The reactor resembles a thin layer evaporator in which the stirrer mixes the gases and at the same time sweeps over the heated walls of the tube reactor to prevent a build-up of polymer material on the wall of the tube. Solid substances would reduce the transfer of heat and cause the reaction to stop. The use of a stirrer rotating at about 1000 revs/min in combination with phosgene at a temperature of about 300° C., however, requires considerable safety precautions to seal off the reactor and to run the stirrer in bearings in the highly corrosive medium.

It has now surprisingly been found that (cyclo)aliphatic diisocyanates may also be prepared in high yield by gas phase phosgenation of the precursor diamines without the disadvantages of the known art processes if certain process parameters to be described in more detail below are observed during the reaction and the gas mixture formed in the reaction is processed by the method also described below.

SUMMARY OF THE INVENTION

The present invention relates to a process for the preparation of diisocyanates corresponding to the formula

OCN—R—NCO wherein
R denotes a (cyclo)aliphatic hydrocarbon group with up to 15 carbon atoms
by phosgenation of the corresponding diamines represented by the formula $H_2N$—R—$NH_2$ in the gas phase, characterized in that
(a) the diamines in vapor form, optionally diluted with an inert gas or with the vapors of an inert solvent, and phosgene are separately heated to temperatures of about 200° to 600° C. and continuously reacted together in a cylindrical reaction chamber which is free from moving parts and heated to about 200° to 600° C., while a turbulent flow is maintained in the reaction chamber,
(b) the gas mixture continuously leaving the reaction chamber is passed through an inert solvent for the diisocyanate which is maintained at a temperature above the decomposition temperature of the carbamic acid chloride corresponding to the diamine, and
(c) the diisocyanate which is dissolved in the inert solvent is purified by distillation.

DETAILED DESCRIPTION OF THE INVENTION

Starting materials for the process according to the invention include the (cyclo)aliphatic diamines corresponding to the formula $H_2N$—R—$NH_2$ wherein
R denotes a (cyclo)aliphatic hydrocarbon group with up to 15, preferably 4 to 13 carbon atoms, at least two carbon atoms being arranged between the two amino groups.

The term "(cyclo)aliphatic" group is used in the present context to denote both aliphatic and cycloaliphatic as well as aliphatic-cycloaliphatic groups and the terms "aliphatic" and "cycloaliphatic" refer to the type of carbon atom linked to the amino groups.

The following are typical examples of suitable diamines: 1,4-diaminobutane, 1,6-diaminohexane, 1,11-diaminoundecane, 1,4-diaminocyclohexane, 1-amino-3,3,5-trimethyl-5-amino-methylcyclohexane (IPDA), 4,4'-diaminodicyclohexylmethane and 4,4'-diaminodicyclohexyl-propane-(2,2). 1,6-diaminohexane, IPDA and 4,4'-diaminodicyclohexylmethane are preferred starting diamines.

Before the process according to the invention is carried out, the starting diamines are vaporized and continuously heated to a temperature within the range of about 200° to 600° C., preferably about 300° to 500° C. The heated diamine vapors may be used in the process according to the invention as such or after dilution with an inert gas or with the vapors of an inert solvent. Mixing of the diamine vapors with the inert gas may be carried out, for example, by vaporizing the diamine in a stream of inert gas or the vapors of an inert solvent. The preferred inert gas is nitrogen. Suitable inert solvents whose vapors may also be used for diluting the diamine include chlorobenzene, o-dichlorobenzene, xylene, chloronaphthalene, decahydronaphthalene and mixtures thereof.

The quantity of inert gas or solvent vapor optionally used as diluent is not critical. Dilution of the diamine may be carried out, for example, with a volumetric ratio of diamine vapor to inert gas or solvent vapor of about 1:0.5 to 1:2.

The phosgene for phosgenation is used in excess, based on the quantity of diamine. It is generally sufficient to use a quantity of phosgene corresponding to about 150–250% of the theoretical amount, based on the phosgenation reaction.

The stream of phosgene is heated to a temperature within the range of about 200° to 600° C., preferably about 300° to 500° C., before the process according to the invention is carried out.

To carry out the reaction according to the invention, the preheated stream of diamine and optionally inert gas or inert solvent vapor and the preheated stream of phosgene are continuously introduced into a cylindrical reaction chamber where they are mixed together.

The cylindrical reaction chambers used may be, for example, tube reactors without any fittings or moving parts inside the reactor. The tube reactors are generally made of steel, glass or alloyed or enamelled steel and are sufficiently long to enable the diamine to react completely with the phosgene under the conditions of the process. The streams of gas are generally introduced into the tube reactor at one end thereof, for example by means of nozzles arranged at one end of the tube reactor or by a combination of a nozzle and an annular gap between the nozzle and the mixing tube. The mixing tube is also kept at a temperature within the range of about 200° to 600° C., preferably about 300° to 500° C., this temperature being maintained by optionally heating the reaction tube.

To enable the process according to the invention to be carried out, it is essential that the dimensions of the tube reactor and the flow velocities inside the reaction chamber should give rise to a turbulent flow inside the reaction chamber. By "turbulent flow" is meant a Reynolds number of at least about 2500, preferably at least about 4700. This turbulence in the reaction chamber is generally ensured if the gaseous reactants flow through the reaction chamber at a velocity of more than about 90 m/s. This flow velocity may be ensured by establishing a suitable pressure difference between the inlet for product into the reaction chamber and the outlet for discharge from the reaction chamber. The pressure in the inlet tubes to the reaction chamber is generally about 200 to 3000 mbar and the pressure at the outlet from the reaction chamber is generally about 150 to 2000 mbar, but the actual pressures are not critical provided that the necessary pressure differential is maintained to ensure the above-mentioned flow velocity.

When phosgenation reaction in the reaction chamber has been terminated, the gaseous mixture continuously leaving the reaction chamber is freed from the diisocyanate formed in the reaction. This may be achieved, for example, by selective condensation in an inert solvent. The temperature of the solvent is so chosen that it lies above the decomposition temperature of the carbamic acid chloride corresponding to the diisocyanate, but still enables the diisocyanate and optionally the solvent used as diluent in vapor form to condense or dissolve in the solvent, respectively, while excess phosgene, hydrogen chloride and any inert gas or optionally solvent used as diluent to flow through the condensation stage. For selective recovery of the diisocyanate from the gaseous mixture leaving the reaction chamber it is particularly suitable to use solvents of the type exemplified above at a temperature of about 120° to 200° C., preferably about 120° to 170° C., in particular commercial dichlorobenzene.

The gas mixture passing through the condensation stage for recovery of the diisocyanate is subsequently freed from excess phosgene in known manner, for example, by means of a cooling trap, absorption in an inert solvent (e.g. chlorobenzene or dichlorobenzene) maintained at a temperature of about $-10°$ C. to 8° C. or adsorption and hydrolysis in contact with activated charcoal. The gaseous hydrogen chloride passing through the phosgene recovery stage may be recycled in a known manner for recovery of the chlorine required for phosgene synthesis.

The diisocyanates are obtained in pure form by distillation of the solution of the diisocyanate in the solvent used for diisocyanate condensation.

All percentages given in the following examples are percentages by weight.

EXAMPLES

Example 1

In a mixing tube heated to 400° C., measuring 2.5 mm in diameter and 17.5 mm in length (having a diisocyanate condensation stage arranged downstream thereof, followed by a phosgene adsorption tower filled with activated charcoal), phosgene which had been heated to 400° C. at a pressure of 1100 mbar in a heat exchanger arranged upstream of the mixing tube flowed continuously into the mixing tube at the rate of 5.91 mol per hour from a nozzle which enters into the mixing tube. At the same time, a mixture, heated to 400° C., of 1.26 mol per hour of gaseous hexamethylene diamine and 1.25 mol per hour of nitrogen was introduced through the annular gap between the nozzle and the mixing tube. A pressure of about 350 mbar was maintained in the mixing tube by the application of a vacuum at the outlet end of the phosgene adsorption tower. Turbulent flow (Reynolds number=10000), was maintained in the reaction chamber through which gases flowed at a velocity of 190 m/s. In the condensation stage, the hot reaction mixture which had left the reaction chamber in gaseous form was passed through dichlorobenzene maintained at a temperature of 150° to 160° C. Selective condensation of the diisocyanatohexane formed took place in this condensation stage. The gas mixture which flowed through the washing stage, consisting mainly of nitrogen, hydrogen chloride and excess phosgene, was subsequently freed from phosgene in the adsorption tower. The diisocyanate was recovered in pure form from the washing solvent by distillation. The yield of 1,6-diisocyanatohexane was 98.0% of the theory.

Example 2

1.26 mol per hour of 1-amino-3,3,5-trimethyl-5-amino-methylcyclohexane were reacted with 5.91 mol per hour of phosgene under the process conditions of Example 1, using 1.25 mol per hour of nitrogen as diluent for the diamine. 1-isocyanato-3,3,5-trimethyl-5- isocyanatomethyl-cyclohexane was obtained in a yield of 99.9%.

Example 3

1.26 mol per hour of 4,4'-diaminodicyclohexylmethane were reacted with 5.91 mol per hour of phosgene under the reaction conditions of Example 1, using 1.25 mol per hour of nitrogen as diluent for the diamine. 4,4'-diisocyanatodicyclohexylmethane was obtained in a yield of 97.8%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a diisocyanate corresponding to the formula

OCN—R—NCO wherein
R denotes a (cyclo)aliphatic hydrocarbon group with up to 15 carbon atoms
by phosgenating a diamine represented by the formula

H$_2$N—R—NH$_2$ in the gas phase, which comprises
(a) separately heating phosgene and said diamine in vapor form, optionally diluted with an inert gas or with the vapors of an inert solvent, to a temperature of about 200° C. to 600° C. and continuously reacting phosgene with said diamine in a cylindrical reaction chamber free from moving parts and heated to about 200° C. to 600° C. while maintaining turbulent flow in the reaction chamber,
(b) passing the gas mixture which continuously leaves the reaction chamber through an inert washing solvent for said diisocyanate, said inert washing solvent being maintained at a temperature above the decomposition temperature of the carbamic acid chloride corresponding to said diamine, and
(c) separating said diisocyanate from said inert washing solvent.

2. The process of claim 1 characterized in that the turbulence in the reaction chamber corresponds to a Reynolds number of at least about 2500.

3. The process of claim 1 wherein said diamine comprises a member selected from the group consisting of 1,6-diaminohexane, 1-amino-3,3,5-trimethyl-5-aminomethylcyclohexane and 4,4'-diaminodicylohexylmethane.

4. The process of claim 2 wherein said diamine comprises a member selected from the group consisting of 1,6-diaminohexane, 1-amino-3,3,5-trimethyl-5-aminomethylcyclohexane and 4,4'-diaminodicylohexylmethane.

5. The process of claim 1 wherein phosgene and said diamine are separately heated to temperatures of about 300° C. to 500° C. and the reaction chamber is maintained at a temperature of about 300° C. to 500° C.

6. The process of claim 1 wherein said inert gas is nitrogen and is present in a ratio by volume of diamine to nitrogen of about 1:0.5 to 1:2.

* * * * *